(12) United States Patent
Khamaisi

(10) Patent No.: US 9,259,170 B2
(45) Date of Patent: Feb. 16, 2016

(54) IMAGING PALLETS FOR MULTI-MODALITY IMAGING SYSTEMS

(75) Inventor: Raed Khamaisi, Haifa (IL)

(73) Assignee: General Electric Company, Schenectady, NY (US)

( * ) Notice: Subject to any disclaimer, the term of this patent is extended or adjusted under 35 U.S.C. 154(b) by 1429 days.

(21) Appl. No.: 12/643,173

(22) Filed: Dec. 21, 2009

(65) Prior Publication Data

US 2011/0152662 A1 Jun. 23, 2011

(51) Int. Cl.
| | | |
|---|---|---|
| A61B 5/05 | (2006.01) | |
| A61B 5/055 | (2006.01) | |
| A61B 6/03 | (2006.01) | |
| A61B 6/04 | (2006.01) | |
| A61B 6/00 | (2006.01) | |
| A61B 5/00 | (2006.01) | |

(52) U.S. Cl.
CPC .............. *A61B 5/0555* (2013.01); *A61B 6/032* (2013.01); *A61B 6/0407* (2013.01); *A61B 6/0457* (2013.01); *A61B 6/0492* (2013.01); *A61B 6/4417* (2013.01); *A61B 6/5235* (2013.01); *A61B 6/5247* (2013.01); *A61B 5/0035* (2013.01); *A61B 6/037* (2013.01); *A61B 6/4258* (2013.01); *A61B 6/508* (2013.01)

(58) Field of Classification Search
USPC .............................................. 5/601; 600/415
See application file for complete search history.

(56) References Cited

U.S. PATENT DOCUMENTS

| | | | |
|---|---|---|---|
| 5,525,905 A * | 6/1996 | Mohapatra et al. ........... 324/318 |
| 6,603,991 B1 * | 8/2003 | Karmalawy et al. .......... 600/411 |
| 6,754,520 B2 * | 6/2004 | DeSilets et al. ............... 600/415 |
| 6,782,571 B1 * | 8/2004 | Josephson et al. ................ 5/601 |
| 6,955,464 B1 * | 10/2005 | Tybinkowski et al. ........ 378/209 |
| 7,170,972 B2 | 1/2007 | Altman |
| 7,357,575 B2 | 4/2008 | Huber et al. |
| 7,412,027 B2 | 8/2008 | Yakubovsky et al. |
| 7,603,730 B2 | 10/2009 | Zelnik |
| 7,613,492 B2 | 11/2009 | Altman et al. |
| 2005/0059877 A1 * | 3/2005 | Falbo, Sr. ...................... 600/407 |
| 2005/0152492 A1 | 7/2005 | Yakubovsky et al. |
| 2005/0207526 A1 | 9/2005 | Altman |
| 2006/0036160 A1 | 2/2006 | Altman et al. |
| 2006/0109959 A1 * | 5/2006 | Kroner et al. ................. 378/209 |
| 2006/0241408 A1 * | 10/2006 | Yakubovsky et al. ......... 600/429 |
| 2007/0053503 A1 | 3/2007 | Zelnik et al. |
| 2007/0080293 A1 | 4/2007 | Huber et al. |
| 2008/0005840 A1 | 1/2008 | Zelnik |
| 2008/0005841 A1 | 1/2008 | Zelnik et al. |
| 2008/0061242 A1 | 3/2008 | Vija et al. |
| 2010/0034350 A1 | 2/2010 | Vaisburd et al. |
| 2011/0092792 A1 * | 4/2011 | Birman ......................... 600/407 |
| 2011/0145991 A1 * | 6/2011 | Bridge et al. ..................... 5/601 |

* cited by examiner

*Primary Examiner* — James Kish
(74) *Attorney, Agent, or Firm* — Dean D. Small; Small Patent Law Group, LLC

(57) ABSTRACT

A multi-modality imaging system including first and second imaging modality units having respective field of views (FOVs) that are spaced apart from each other. The imaging system also having a positioning system that includes an imaging pallet. The pallet has an elongated support body that includes first and second portions that extend lengthwise along the support body. The first portion is shaped for imaging within the FOV of the first modality unit, and the second portion is shaped for imaging within the FOV of the second modality unit. The first and second portions are shaped differently than each other. The positioning system is configured to position the first portion of the pallet within the FOV of the first modality unit and configured to position the second portion of the pallet within the FOV of the second modality unit.

22 Claims, 9 Drawing Sheets

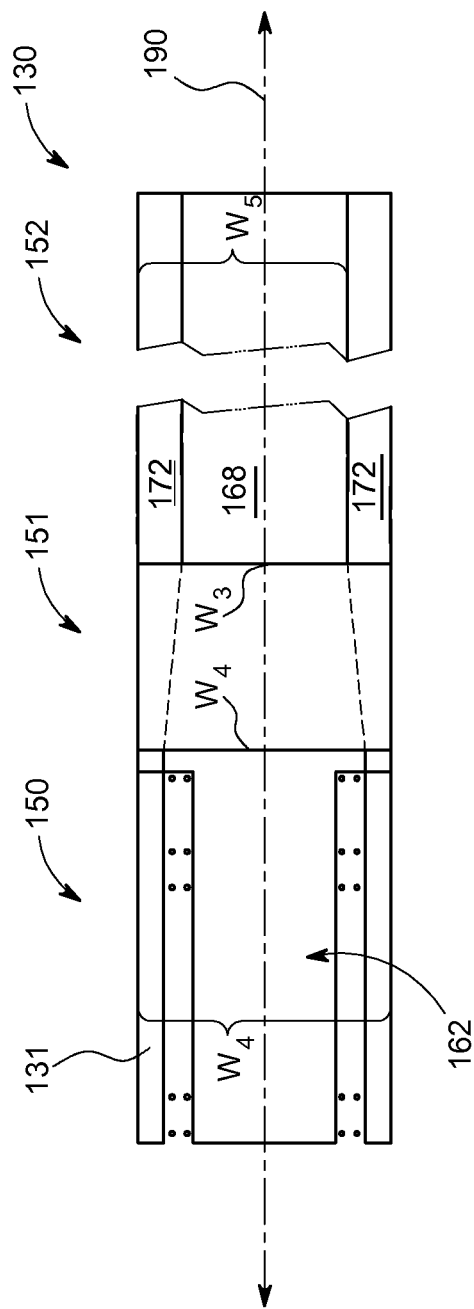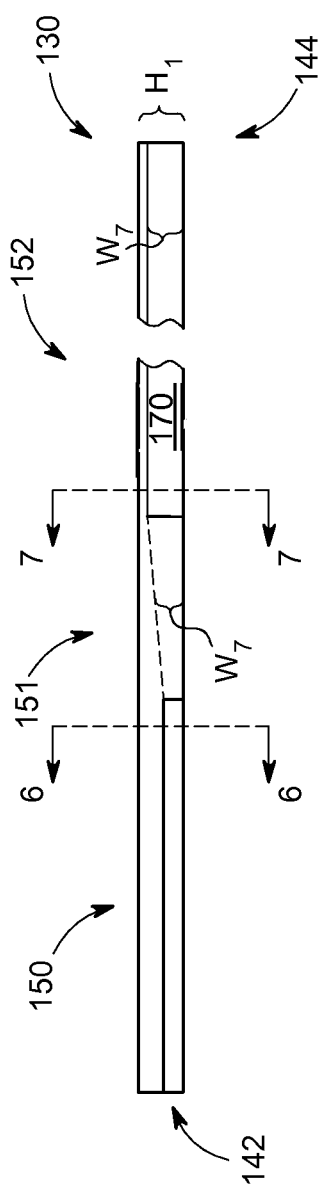

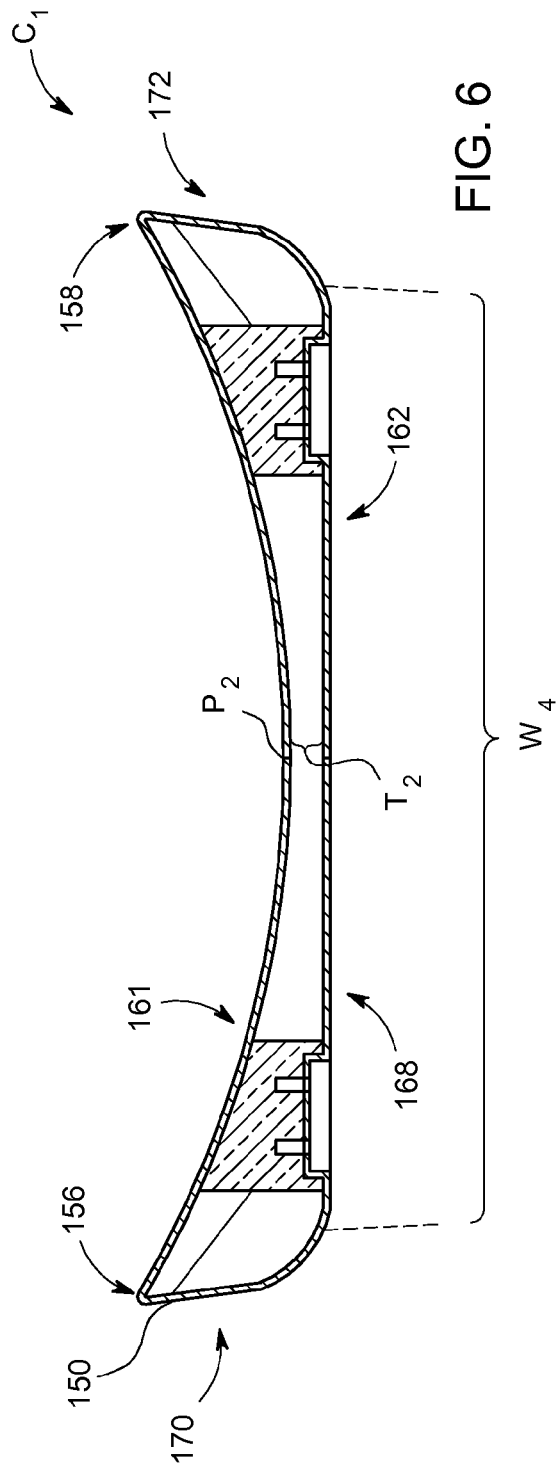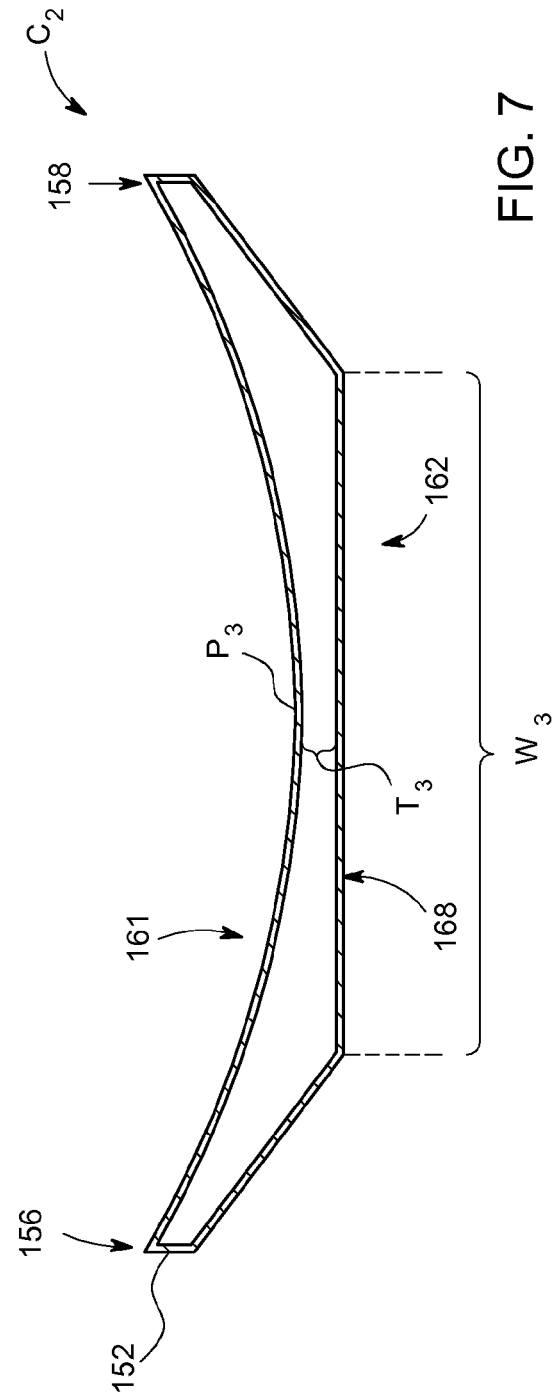

IMAGING PALLETS FOR MULTI-MODALITY IMAGING SYSTEMS

BACKGROUND OF THE INVENTION

The subject matter disclosed herein relates generally to multi-modality imaging systems and more particularly, to imaging pallets for multi-modality imaging systems.

Multi-modality imaging systems can scan one or more regions of interest (ROI) of a patient using different imaging modalities. Multi-modality imaging systems may include Computed Tomography (CT), Magnetic Resonance Imaging (MRI), Positron Emission Tomography (PET), radiography imaging, x-ray imaging, and/or Single Photon Emission Computed Tomography (SPECT) imaging systems, among others. By way of example, in some multi-modality imaging systems, the different modality units may have respective field of views (FOVs) at different axial locations along an examination axis. During operation, a patient is moved to a first FOV where an image of the ROI is obtained with a first imaging modality unit and then moved to a second FOV where another image of the ROI is obtained using a second imaging modality unit. A doctor or medical technician (or the system) may then review or combine the images from the different modalities.

Depending upon the imaging modality being used, certain geometries of the pallet may cause artifacts within the images. To address this challenge, imaging systems may use a separate pallet for positioning within each type of imaging modality. However, this can be costly and require extra time for a technician to change the pallets.

In other multi-modality imaging systems, a common pallet is used for the different imaging modalities. One advantage in using one common pallet is that the patient does not move with respect to the common pallet. Motion controllers and position encoders may be used to register the position of the pallet during each image acquisition to enable accurate and automatic registration of the images taken with the different modalities. However, the common pallet may not be optimally designed for all of the imaging modalities thereby affecting imaging quality.

BRIEF DESCRIPTION OF THE INVENTION

In one embodiment, a multi-modality imaging system is provided that includes first and second imaging modality units having respective field of views (FOVs) that are spaced apart from each other. The imaging system also has a positioning system that includes an imaging pallet. The pallet has an elongated support body that includes first and second portions that extend lengthwise along the support body. The first portion is shaped for imaging within the FOV of the first modality unit, and the second portion is shaped for imaging within the FOV of the second modality unit. The first and second portions are shaped differently than each other. The positioning system is configured to position the first portion of the pallet within the FOV of the first modality unit and configured to position the second portion of the pallet within the FOV of the second modality unit.

In another embodiment, an imaging pallet for an imaging system is provided. The pallet includes an elongated support body that is adapted to support a patient thereon during an imaging session. The support body has a length that extends between opposite ends of the support body. The pallet includes a mounting portion of the support body that extends along the length. The mounting portion is configured to engage a positioning system of the imaging system. The pallet also includes a first portion of the support body that extends lengthwise away from the mounting portion. The first portion is shaped for imaging with a first type of imaging modality. The pallet further includes a second portion of the support body that extends along the length. The first portion extends between the mounting and second portions. The second portion is shaped for imaging with a second type of imaging modality. The first and second portions having different shapes.

In a further embodiment, a method of operating a multi-modality imaging system is provided. The imaging system includes a positioning system that is configured to move patients on an imaging pallet and first and second imaging modality units having respective field of views (FOVs). The method includes positioning a region-of-interest (ROI) of a first patient on a middle portion of the pallet of the positioning system and scanning the ROI of the first patient within the FOV of the first modality unit. The middle portion is shaped for imaging with the first modality unit. The method also includes positioning a ROI of a second patient on a distal portion of the pallet and scanning the ROI of the second patient at one of the FOVs of the first and second modality units. The distal portion is shaped differently than the first portion.

BRIEF DESCRIPTION OF THE DRAWINGS

FIG. 4 is a bottom view of the pallet shown in FIG. 3.

FIG. 5 is a side view of the pallet shown in FIG. 3.

FIG. 6 is a cross-sectional view of the pallet taken along a line 6-6 shown in FIG. 5.

FIG. 7 is a cross-sectional view of the pallet taken along a line 7-7 shown in FIG. 5.

DETAILED DESCRIPTION OF THE INVENTION

The foregoing summary, as well as the following detailed description of certain embodiments of the present invention, will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" or "an embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
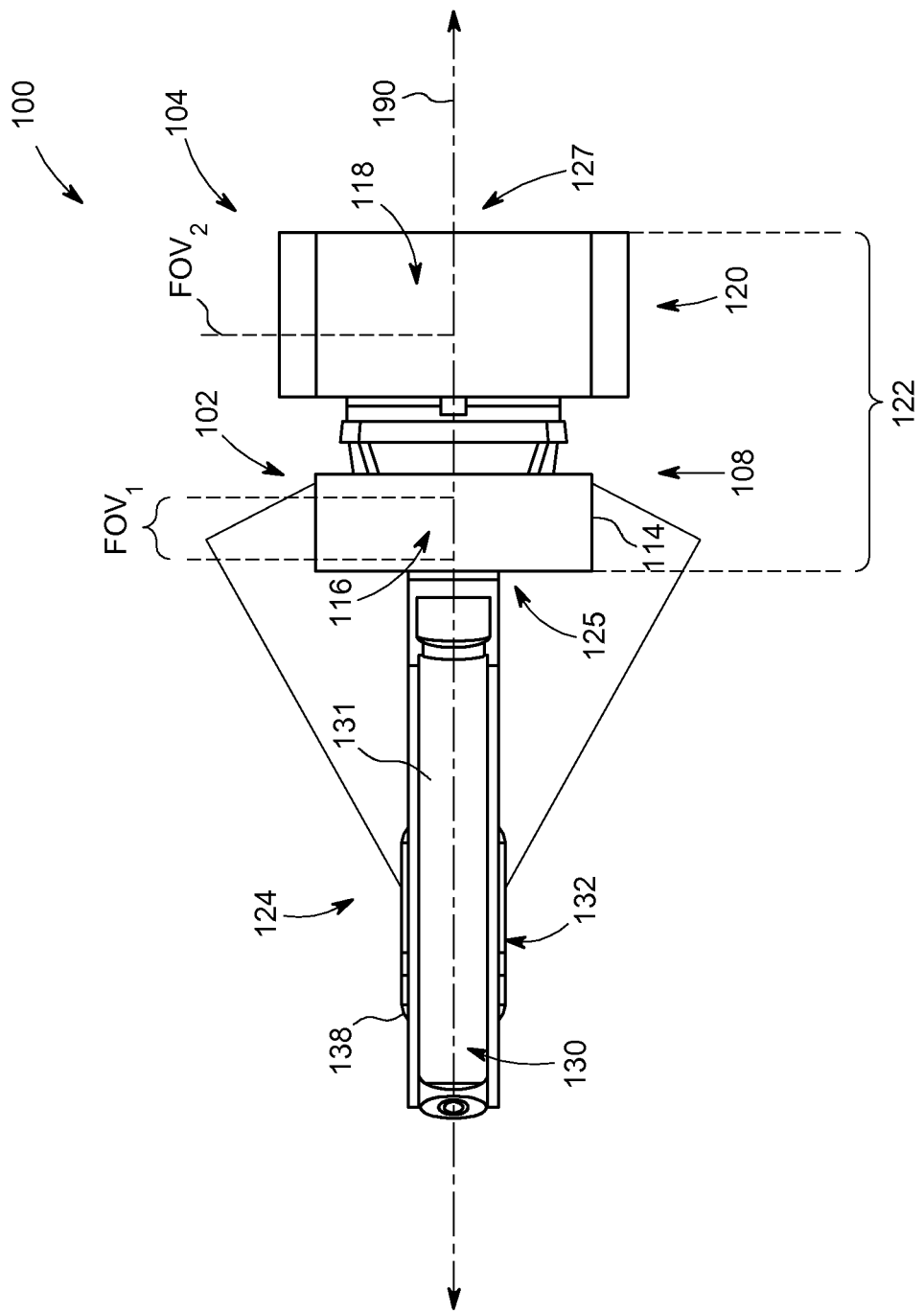
FIG. 1 is a top plan view of a multi-modality imaging system formed in accordance with various embodiments.

FIG. 1 is a top plan view of a multi-modality imaging system formed in accordance with various embodiments. The imaging system 100 may include different types of imaging modality units, such as a Positron Emission Tomography (PET) modality unit, a Single Photon Emission Computed Tomography (SPECT) modality unit, a Computed Tomography (CT) modality unit, a Magnetic Resonance Imaging (MRI) modality unit, X-Ray radiography or fluoroscopy modality unit, an ultrasound modality unit, and/or any other modality unit(s) capable of generating images of a region of interest (ROI). In particular embodiments, the imaging system 100 is a medical imaging system. However, the various embodiments are not limited to medical imaging systems for imaging human subjects, but may include veterinary systems as well as non-medical imaging systems. As used herein, the term "patient" may refer to a human patient or any other animal.

Referring to FIG. 1, the imaging system 100 is a multi-modality medical imaging system that includes a first imaging modality unit 102 and a second imaging modality unit 104. The first and second modality units 102 and 104 enable the imaging system 100 to scan a patient (not shown) in a first type of modality using the first modality unit 102 and to also scan the patient in a second type of modality using the second modality unit 104. The first and second modality units 102 and 104 may be located adjacent to each other, attached, and/or enclosed within a common housing. In some embodiments, the multi-modality imaging system 100 may include multiple single modalities that are positioned at different locations. The imaging system 100 allows for multiple scans in different modalities to facilitate an increased diagnostic capability over single modality systems. In one embodiment, the medical imaging system 100 is a Computed Tomography/Nuclear Medicine (CT/NM) imaging system. For example, the first modality unit 102 may be an NM imaging system (e.g., SPECT) and the second modality unit 104 may be a CT imaging system.

Figure 2:
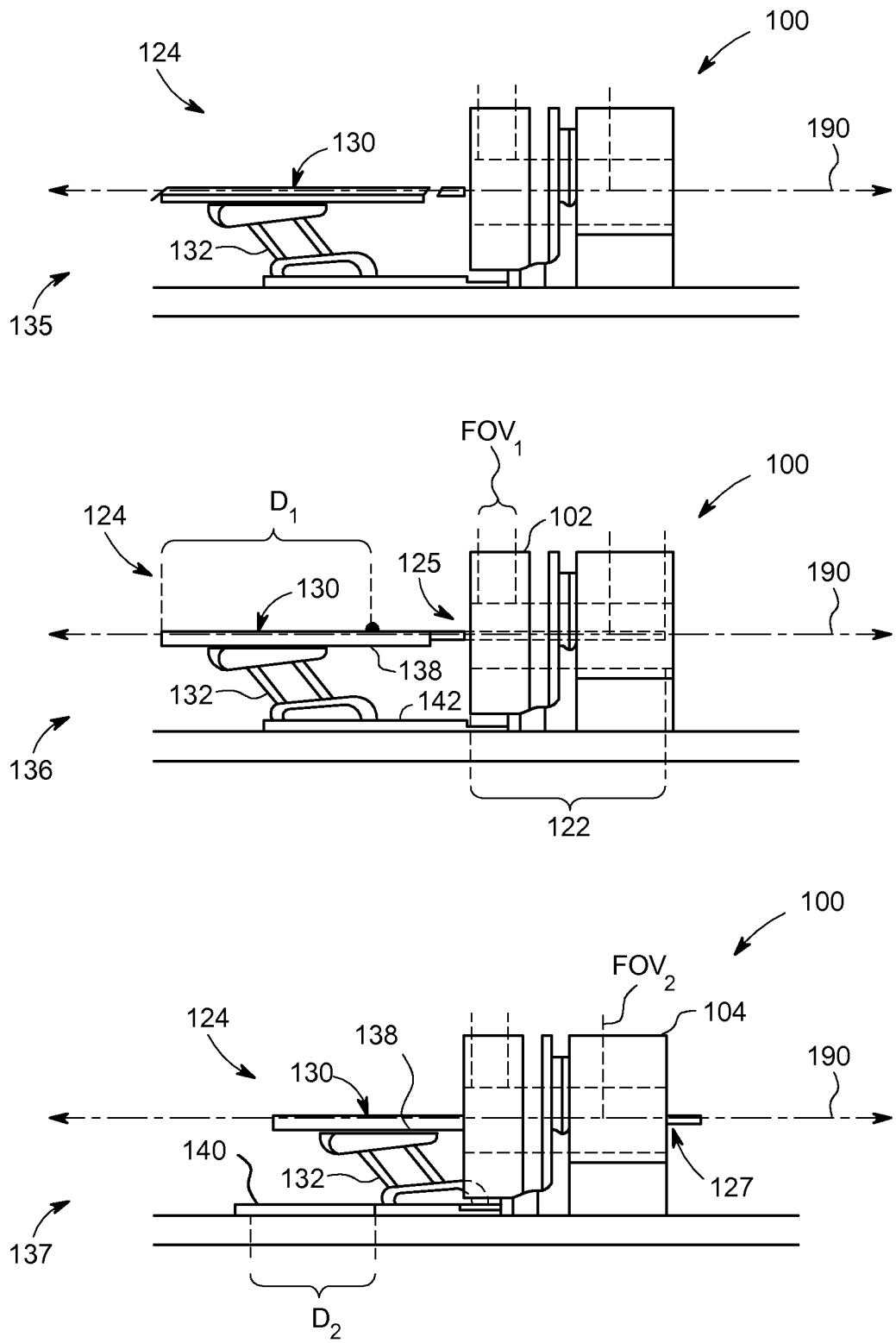
FIG. 2 is a diagram illustrating various stages of a positioning system formed in accordance with various embodiments that may be used with the imaging system of FIG. 1.

The imaging system 100 is also shown as including a gantry 108 that is associated with the first modality unit 102 and a gantry 120 that is associated with the second modality unit 104. The gantry 108 includes a rotor 114 that supports, for example, NM cameras, which may be gamma cameras, SPECT detectors, and/or PET detectors. The rotor 114 may be configured to rotate the NM cameras about an examination axis 190 that may extend through a center of one or more bores of the imaging system 100. More specifically, the gantry 108 may include a bore 116, and the gantry 120 may include a bore 118. The bores 116 and 118 may be aligned along the examination axis 190 as shown in FIG. 2. Furthermore, the bores 116 and 118 may collectively form a common bore 122 for the imaging system 100 such that the common bore 122 begins at an opening 125 of the bore 116 and ends at an exit 127 of the bore 118. Each bore is sized and shaped to allow a patient to be moved into and out of the bore along the examination axis 190. In some embodiments, each bore may be sized and shaped differently or, alternatively, have a common cross-sectional size.

The imaging system 100 also includes a patient positioning system 124 (also referred to as a table system) for moving the ROI of the patient to an axial location or position along the examination axis 190. The positioning system 124 may include an imaging pallet 130 that is adapted to support a patient thereon. The pallet 130 has an elongated support body 131 that extends in a direction along the examination axis 190. In some embodiments, the pallet 130 may be referred to as a couch, a cradle, a bed, or a table. Moreover, the positioning system 124 may include a system base or pedestal 132 and a pallet support 138 that is operatively coupled to the pallet 130. For example, the pallet 130 may be movably or slidably engaged to the pallet support 138, which may be supported by the system base 132. During operation of the imaging system 100, the positioning system 124 may selectively move the patient in an axial direction (e.g., in a direction along the examination axis 190) into and through the central opening 125 of the bore 122. In some embodiments, the positioning system 124 may also move the pallet 130 up-down in a vertical manner or side-to-side in a lateral manner. The positioning system 124 is configured to position the patient within one or more field-of-views (FOVs) of the imaging system 100.

During an imaging session, energy transmitted through a FOV or emitted from a patient in a FOV (e.g., from a decaying radionuclide injected into a patient) may be detected by the imaging modality unit. The energy may not only be affected by the patient, but may also be affected by the portion of the pallet within the FOV. This affect may be at least partially based upon a material of the portion of the pallet within the FOV and a geometry or shape of the portion of the pallet within the FOV. Furthermore, geometries and/or materials may have different effects on different types of imaging modalities. For example, a specific geometry or shape of the pallet may be better (e.g., provide less attenuation) for a first type of imaging modality than for a second type of imaging modality.

As will be described in greater detail below, the pallet 130 may have different body portions along a length of the pallet 130 that are configured for use with or in different modality units. For example, a body portion that is configured for a first type of imaging modality may provide less energy attenuation or fewer artifacts in an image than other body portions for the first type of imaging modality. As another example, in a multi-modality imaging system where a first body portion is configured or shaped for a first imaging modality unit and a second body portion is configured or shaped for a second imaging modality unit, the first body portion provides less attenuation or fewer artifacts than the second body portion with respect to the first imaging modality unit and the second body portion provides less attenuation or fewer artifacts than the first body portion with respect to the second imaging modality unit.

However, the geometry or shape and/or material of a body portion that is configured or shaped for a type of imaging modality is not required to be ideal or optimal for embodiments described herein. A body portion may be "configured for" or "shaped for" imaging within a type of imaging modality if the body portion provides, for example, an acceptable level of energy attenuation or an acceptable amount of artifacts in an image.

FIG. 2 illustrates the imaging system 100 at various stages 135-137 in which the positioning system 124 has been moved to different axial locations or positions along the examination axis 190. At stage 135, the positioning system 124 is in a loading position. In the loading position, the patient may be positioned onto the pallet 130. Furthermore, in the loading position, accessories (e.g., headrests, leg supports, belts, and the like) may be attached to the positioning system 124 or, more specifically, the pallet 130. In addition, the pallet 130 may be replaced or substituted with a different pallet (e.g., for maintenance or refurbishing).

At stage 136, the pallet 130 has been moved in an axial direction (e.g., along the examination axis 190) through the opening 125 and into the bore 122. The pallet 130 may be selectively moved by the positioning system 124 along the pallet support 138 such that the system base 132 remains stationary. In other words, the pallet 130 may be independently movable with respect to the system base 132 and the pallet support 138.

The pallet 130 may be moved to various positions with respect to the pallet support 138. For example, as shown in FIG. 2 at stage 136, the pallet 130 is moved an axial distance $D_1$ to approximately a fully-extended position with respect to the pallet support 138. Alternatively or in addition to, the pallet 130 may be selectively moved by moving the system base 132 along a platform 140 of the positioning system 124. As such, a predetermined portion of the pallet 130 may be located within the $FOV_1$ of the first modality unit 102. Furthermore, the pallet 130 may be selectively moved by the positioning system 124 so that a predetermined ROI of the patient is located within the $FOV_1$ of the first modality unit 102. The ROI of the patient may then be scanned by the first modality unit 102. As such, stage 136 may also be referred to as a first scan position.

At stage 137, the pallet 130 has been moved in an axial direction through the bore 122 toward the exit 127 and toward the $FOV_2$ of the second modality unit 104. Similar to above, the pallet 130 may be selectively moved by the positioning system 124 along the pallet support 138 of the positioning system 124 such that the system base 132 remains stationary. However, if the pallet 130 has been fully extended as shown in FIG. 2, the system base 132 may be selectively moved along the platform 140 an axial distance $D_2$. As such, a predetermined portion of the pallet 130 may be located within the $FOV_2$ of the second modality unit 104. Likewise, the pallet 130 may be selectively moved by the positioning system 124 so that a predetermined ROI of the patient is located within the $FOV_2$ of the second modality unit 104. The ROI of the patient may then be scanned by the second modality unit 104. As such, stage 137 may also be referred to as a second scan position.

Although the imaging system 100 is shown as having two modality units, the imaging system 100 may have three or more modality units in alternative embodiments. In particular embodiments, the imaging system 100 has only two modality units. In other particular embodiments, the imaging system 100 has only three modality units.

Furthermore, in the illustrated embodiment shown in FIG. 2, the imaging system 100 has two FOVs that are aligned with respect to each other along the examination axis 190. By way of example, the $FOV_1$ may extend along the examination axis 190 a distance of about 15-40 cm, and the $FOV_2$ may extend along the examination axis 190 a distance of about 2-10 cm. In alternative embodiments, the multi-modality system may include separate modality units that are not aligned or positioned adjacent to each other. For example, after scanning a patient with a first modality unit, the pallet may be retracted to the loading position and then rotated, e.g., 90° about a vertical axis (not shown) to face a second modality unit. The pallet may then be moved into the second modality unit for a second scan.

As can be seen at stage 137 where the pallet 130 is extended into the imaging system 100, a portion of the pallet 130 is located to the left of $FOV_2$ of the second modality unit 104 and does not enter into the $FOV_2$. Thus, this portion of the pallet 130 is never imaged by the second modality unit 104 and does not need to be configured for imaging by the second modality unit 104. Similarly, a portion of the pallet 130 is located to the left of $FOV_1$ of the first modality unit 102 and does not enter the $FOV_1$ or the $FOV_2$. Thus, this portion of the pallet 130 is never imaged by any modality unit and does not need to be configured for imaging at all. This portion of the pallet 130 may be configured for different purposes, such as support or mounting. Additionally, a portion of the pallet 130 which is located to the left of $FOV_2$ but to the right of $FOV_1$ can be imaged by the first modality unit 102, and thus may be configured for imaging by the first modality unit only. In contrast, a portion of the pallet 130 located to the left of the $FOV_2$ may be imaged by both the first modality unit 102 and the second modality unit 104. This portion may be configured for imaging by both types of modalities. The various portions described above may be, for example, the body portions 150-152 which are described in greater detail below.

Figure 3:
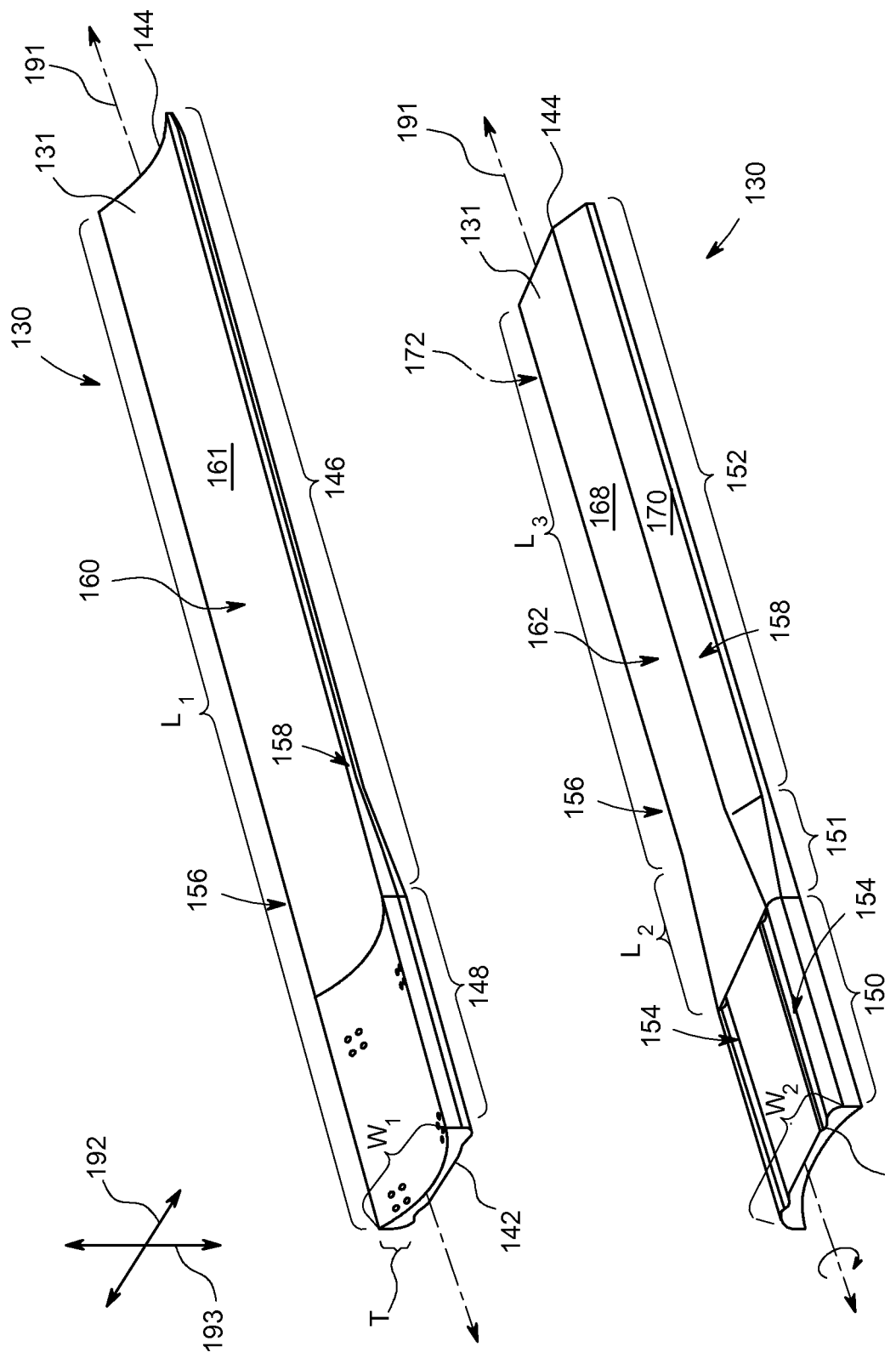
FIG. 3 are perspective views of an imaging pallet formed in accordance with various embodiments.

FIG. 3 shows top and bottom perspective views of the pallet 130. The pallet 130 is shown as being oriented with respect to a longitudinal axis 191, a lateral axis 192, and a vertical axis 193. When oriented in the imaging system 100 (FIG. 1), the longitudinal axis 191 extends along the examination axis 190 (FIG. 1). The support body 131 of the pallet 130 extends in a direction along the longitudinal axis 191. The support body 131 has opposite ends 142 and 144 and a pallet length $L_1$ extending therebetween. The support body 131 also has a width $W_1$ measured along the lateral axis 192 that extends between edges 156 and 158. In the illustrated embodiment, the width $W_1$ is substantially uniform throughout the pallet length $L_1$. In other embodiments, the width $W_1$ may change or vary as desired.

The pallet 130 may include a scan region 146 and a non-scan region 148. The scan region 146 of the pallet 130 is capable of being positioned within the bore 122 (FIG. 1) during an imaging session and is configured to support the ROI of the patient when imaged by one of the modality units 102 and 104. The non-scan region 148 is typically not within the bore 122 during an imaging session. The scan and non-scan regions 146 and 148 may comprise different materials and/or have different configurations. The non-scan region 148 may be constructed to attach to and move along the pallet support 138, and the scan region 146 may be generally formed for reduced attenuation during an imaging session.

As shown in FIG. 3, the pallet 130 may include a support or patient side 160 that is adapted to support a patient thereon, and a mounting or bottom side 162. The pallet 130 may also have a thickness $T_1$ extending therebetween. The patient side 160 has a support surface 161 that extends between the ends 142 and 144. In the illustrated embodiment, the support surface 161 has a curved contour configured to cradle or hold the patient in a predetermined position. However, in alternative embodiments, the support surface 161 may be substantially flat or planar. Furthermore, in some embodiments, the support surface 161 is substantially continuous throughout the scan region 146. However, the support surface 161 is not required to be substantially continuous and may have one or more broken areas that effectively separate the surfaces into two portions. In other embodiments, the support surface 161 is substantially continuous throughout the patient side 160 between the ends 142 and 144 as shown in FIG. 3.

The bottom side 162 has a bottom surface 168 and edge or side surfaces 170 and 172. The bottom surface 168 may be substantially continuous throughout the scan region 146 as the bottom surface 168 extends between the ends 142 and 144. In the illustrated embodiment, the bottom surface 168 may be substantially planar. The side surfaces 170 and 172 may extend between and join the bottom surface 168 and the support surface 161 at edges 156 and 158.

Also shown in FIG. 3, the pallet 130 includes a plurality of body portions 150-152. Each body portion 150-152 may have a different composition with respect to other body portions and/or may have different geometries or shapes. As used herein, body portions are shaped differently if the body portions have different dimensions or geometries in respective cross-sections taken transverse to the longitudinal axis 191 (e.g., cross-sections taken along a plane parallel to the lateral and vertical axes 192 and 193). For example, the cross-sections may have one or more different dimensions (e.g., height, width) or geometries (e.g., curvature of surface, angles formed between two different surfaces).

The pallet 130 shown in FIG. 3 illustrates one exemplary embodiment. The non-scan region 148 may include a mounting portion 150 that is configured to be coupled to (e.g., mounted or attached) to the pallet support 138 (FIG. 1). The mounting portion 150 may include, for example, slots 154 that extend along the longitudinal axis 191 of the pallet 130 from the end 142. The slots 154 may be reinforced by steel inserts.

The pallet 130 may also include a middle (or first) portion 151 and a distal (or second) portion 152. The middle portion 151 and the distal portion 152 may be sized and shaped for different types of imaging modalities. In the illustrated embodiment, the middle portion 151 extends from the mounting portion 150 toward the distal portion 152. The distal portion 152 extends to the end 144. The middle portion 151 may have a portion length $L_2$, and the distal portion 152 may have a portion length $L_3$. In the illustrated embodiment, the length $L_3$ is greater than the length $L_2$ and may be greater than ½ of the length $L_1$. However, in alternative embodiments, the body portions 150-152 may have other lengths.

In the exemplary embodiment, the middle portion 151 may be used with NM imaging modality units, and the distal portion 152 may be used with both CT and NM imaging modality units. In particular embodiments, the attenuation of the middle portion 151 to 140 keV gamma rays may not exceed 10%. In particular embodiments, the attenuation of the distal portion 152 to 120 kVp X-ray may not exceed 27%.

As used herein, the terms "mounting," "middle," and "distal" or the terms "first," "second," and "third" are only used to distinguish the different body portions within the pallet and are not intended to limit the scope of embodiments herein. For instance, the pallet may include only two body portions. By way of example, a first portion in such an embodiment may be mounted to the pallet support 138 and also extend a distance that allows the first portion to be imaged by an imaging modality. Furthermore, the pallet may include more than three body portions. By way of example, a pallet may include a mounting portion, two middle portions, and a distal portion. Furthermore, terms that are used to distinguish the body portions do not necessarily indicate an order of the body portions or positions with respect to each other.

In addition, body portions are not required to be configured for imaging within a certain type of imaging modality. Alternatively or additionally, a body portion may function as a transition region where the pallet changes from one shape into another shape. Such a transition region may or may not be suitable for an imaging modality. For example, a pallet may include a series of body portions that includes a first portion that is configured for use with a first type of imaging modality, a second portion that functions as a transition region, and a third portion that is configured for use with another type of imaging modality. In this case, the second portion may function exclusively as a transition region where the pallet changes from the first portion to the third portion.

In some embodiments, the pallet 130 has a sandwich construction that includes a foam core having an outer surface that includes a composite skin (e.g., carbon fiber, fiberglass, Kevlar®). The composite skin may be bonded to at least some of the outer surface. The foam core may be, for example, polyurethane and, more specifically, polyurethane at 7 lb/ft. In other embodiments, the body portions 150-152 may comprise different materials and/or have different amounts/densities of materials. For example, the middle and distal portions 151 and 152 within the scan region may have different materials that are configured for the respective imaging modality units. If one imaging modality unit is an MRI-type modality, materials for the corresponding portion of the pallet may be substantially non-magnetic. In another imaging modality unit, materials may be configured so that decaying radionuclides injected into a patient may be detected.

FIG. 4 is a bottom view of the pallet 130 illustrating the bottom side 162 and the side surfaces 170 and 172 for the middle and distal portions 151 and 152. The bottom side 162 has different widths $W_2$ and $W_3$ at the middle portion 151 measured along the bottom surface 168 and perpendicular to the longitudinal axis 191. The widths $W_2$ and $W_3$ are spaced apart along the longitudinal axis 191. For example, the width $W_2$ is measured proximate to the mounting portion 150, and the width $W_3$ is measured proximate to the distal portion 152. As shown, the width W of the bottom side 162 at the middle portion 151 reduces as the middle portion 151 extends from the mounting portion 150 toward the distal portion 152. Furthermore, in the illustrated embodiment, the bottom side 162 has a width $W_4$ along the mounting portion 150 that is substantially uniform throughout the mounting portion 150. Likewise, in the illustrated embodiment, the bottom side 162 has a width $W_5$ along the distal portion 152 that is substantially uniform throughout the distal portion 152. The width $W_5$ may be less than the width $W_1$ (FIG. 3) of the pallet 130. However, in alternative embodiments, the widths $W_4$ and $W_5$ may vary throughout the mounting portion 150 and the distal portion 152, respectively.

FIG. 5 is a side view of the pallet 130 illustrating the side surface 170. As shown, the pallet 130 has a height $H_1$. In the illustrated embodiment, the height $H_1$ is substantially uniform throughout the support body 131. However, in alternative embodiments, the height $H_1$ may vary. For example, the height $H_1$ may slowly decrease as the pallet extends from end 142 to end 144. Also shown in FIG. 5, the side surface 170 has a width $W_6$ along the middle portion 151 and a width $W_7$ along the distal portion 152. In the illustrated embodiment, the width $W_6$ increases as the middle portion 151 extends from the mounting portion 150 toward the distal portion 152, and the width $W_7$ is substantially uniform throughout the distal portion 152.

FIGS. 6 and 7 illustrate exemplary cross-sections $C_1$ and $C_2$ taken along the lines 6-6 and 7-7 shown in FIG. 5. The cross-sections $C_1$ and $C_2$ are taken through the mounting portion 150 and the distal portion 152, respectively. The cross-section $C_1$ may also represent a cross-section within the middle portion 151 that is proximate to the mounting portion 150. As such, the cross-section $C_1$ may be referred to as a medial cross-section. The cross-section $C_2$ may also represent a cross-section within the middle portion 151 that is proximate to the distal portion 152. As such, the cross-section $C_2$ may be referred to as a distal cross-section. The medial and distal cross-sections may have different dimensions or geometries.

As will be explained in greater detail below, the cross-sections $C_1$ and $C_2$ may have different dimensions or geometries such that a shape of the middle portion 151 changes as the middle portion 151 extends between the cross-sections $C_1$ and $C_2$. Accordingly, the middle portion 151 has dual-functions in the illustrated embodiment. The middle portion 151 may be configured for imaging within the $FOV_1$ of the first modality unit 102, and the middle portion 151 may function as a transition region where a shape of the middle portion 151 changes as the middle portion 151 extends between other body portions, such as the mounting portion 150 and the distal portion 152.

With respect to FIG. 6, the support surface 161 in the mounting portion 150 may have a curved contour. The curved contour may be uniform such that the curved contour maintains a radius-of-curvature through the cross-section $C_1$. The radius-of-curvature may be with respect to a center (not shown) that is located on an axis (not shown) that is parallel to the longitudinal axis 191 (FIG. 3). With respect to FIG. 7, the support surface 161 in the distal portion 152 may also have a curved contour. The curved contour may also be uniform such that the curved contour maintains a radius-of-curvature through the cross-section $C_1$. In the illustrated embodiment, the radius-of-curvature for the distal portion 152 is substantially equal to the radius-of-curvature for the mounting portion 150. Accordingly, the support surface 161 has a radius-of-curvature that is substantially uniform throughout the scan region 146. In particular embodiments, the radius-of-curvature is substantially uniform throughout the entire pallet 130 between the ends 142 and 144.

Also shown in FIGS. 6 and 7, the support surface 161 extends from the edges 156 and 158 to a lowest point or trough (indicated as point $P_2$ for the mounting portion 150 and as point $P_3$ for the distal portion 152). A thickness $T_2$ of the mounting portion 150 may be measured from the lowest point $P_2$ to the bottom surface 168. Likewise, a thickness $T_3$ of the distal portion 152 may be measured from the lowest point $P_3$ to the bottom surface 168. As shown in FIGS. 6 and 7, the thicknesses $T_2$ and $T_3$ are substantially equal. Accordingly, as the trough or lowest point of the support surface 161 extends lengthwise through the middle and distal portions 151 and 152, the pallet 130 may have a thickness T measured between the lowest point and the bottom surface 168 that is substantially uniform throughout the middle and distal portions 151 and 152. In some embodiments, the thickness T measured between the lowest point and the bottom surface 168 along the support surface 161 is substantially uniform throughout the scan region 148.

Figure 8:
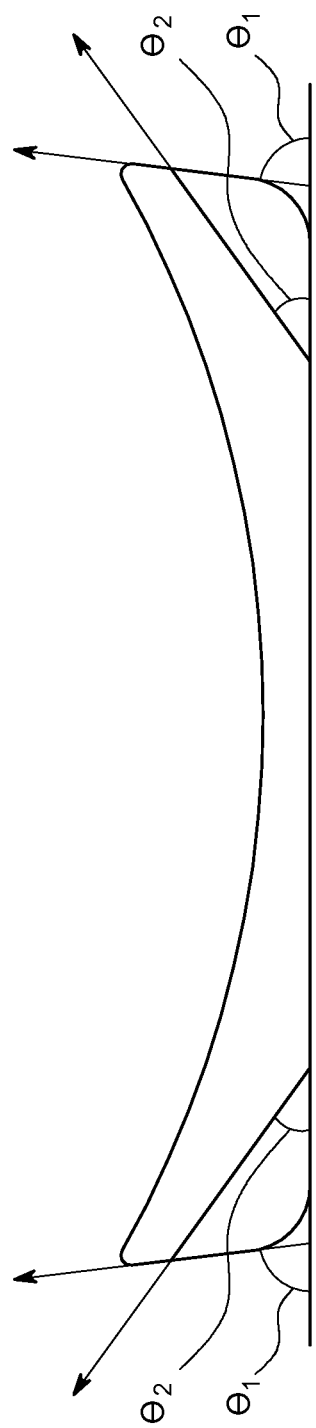
FIG. 8 illustrates a comparison of the shapes of the cross-sections shown in FIGS. 6 and 7.

FIG. 8 illustrates a comparison of the cross-sections $C_1$ and $C_2$ shown in FIGS. 6 and 7. As described above, in the illustrated embodiment, the curved contour of the scan region 146 may be substantially uniform as the pallet 130 extends toward the end 144. However, the side surfaces 170 and 172 may not be uniform. As shown in FIG. 8, the side surfaces 170 and 172 of the mounting portion 150 may project away from the bottom surface 168 at an angle $\theta_1$. However, the side surfaces 170 and 172 along the distal portion 152 may project away from the bottom surface 168 at an angle $\theta_2$. The angle $\theta_2$ may be less than the angle $\theta_1$. Accordingly, as the pallet 130 extends toward the distal portion 152, the angle $\theta$ measured between the corresponding side surface and a plane of the bottom surface 168 may decrease. During the decrease in the angle $\theta$, the width W of the bottom side 162 may decrease or reduce from the width $W_4$ to the width $W_3$.

Figure 9:
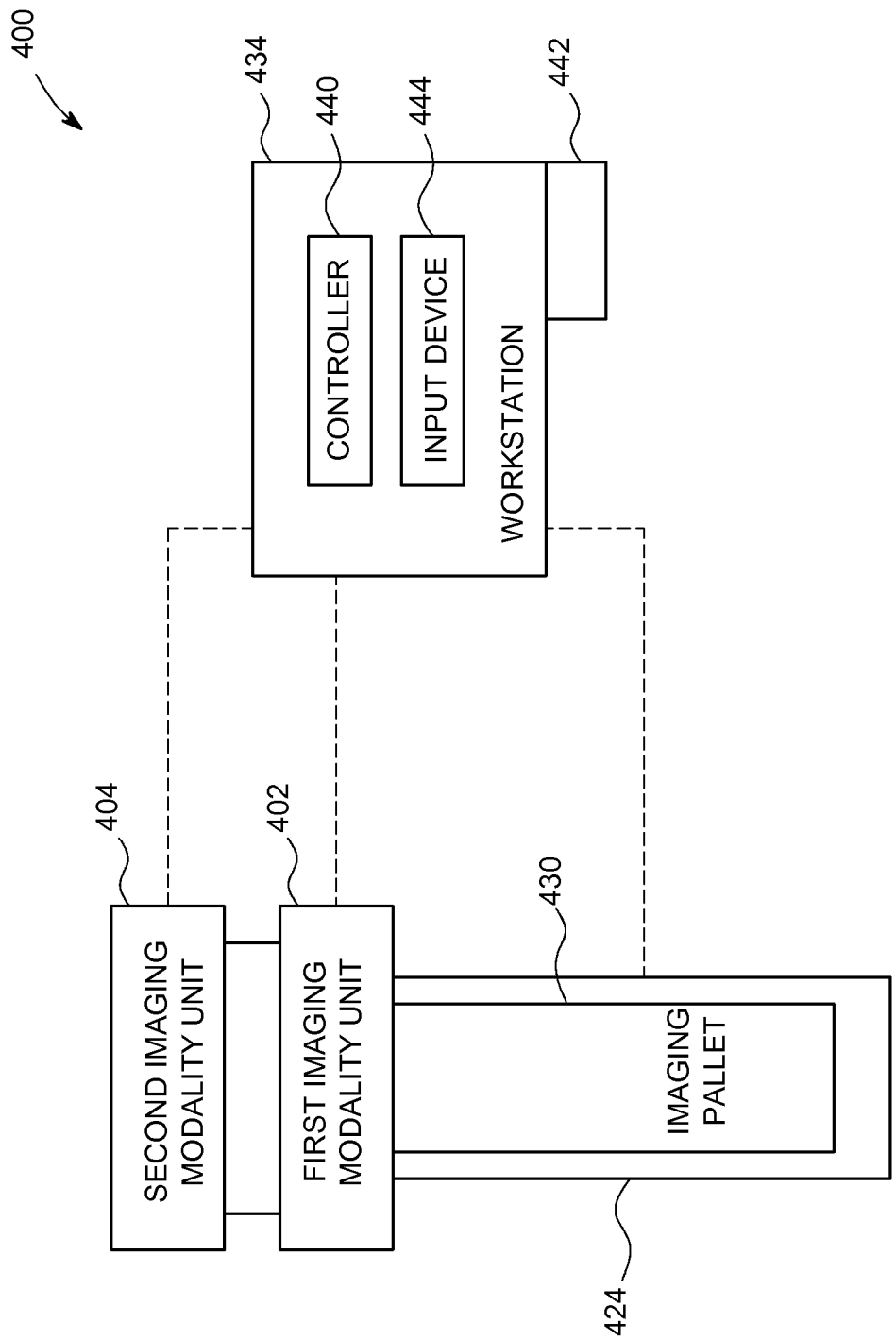
FIG. 9 is a schematic diagram of a multi-modality imaging system formed in accordance with various embodiments.

FIG. 9 is a block schematic diagram of a multi-modality imaging system 400 that may be similar to the imaging system 100 illustrated in FIG. 1. The imaging system 400 may include a workstation 434 that is communicatively coupled to first and second modality units 402 and 404 and a positioning or table system 424 through one or more communication links (indicated as dashed lines). The first and second modality units 402 and 404 may be of different types as described above. The positioning system 424 includes an imaging pallet 430. The pallet may include features similar to the pallet 130 described above. The communication links may be hardwired and/or wireless communication links. The workstation 434 may be, for example, a personal computer, laptop computer, or a handheld device. In the exemplary embodiment, the workstation 434 controls real-time operation of the components of the imaging system 400. The workstation 434 may also be programmed to perform medical image diagnostic acquisition and reconstruction processes.

The workstation 434 includes a central processing unit (CPU) or controller 440, a display 442 and an input device 444. As used herein, the term "controller" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. In the exemplary embodiment, the controller 440 executes a set of instructions that are stored in one or more storage elements or memories, in order to process input data, which may be user inputs. The storage elements may also store data or other information as desired or needed. The storage element may be in the form of an information source or a physical memory element within the controller 440 and/or within the workstation 434.

The set of instructions may include various commands that instruct the controller 440 as a processing machine to perform specific operations such as methods and processes of various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The controller 440 receives user inputs, e.g., user commands, from the input device 444. The input device 444 may be, for example, at least one of a keyboard, mouse, a touch-screen panel, a voice recognition system, and the like. An operator may control the operation of the imaging system 400 through the input device 444. More specifically, an operator may control the positioning system 424 and the first and second modality units 402 and 404 to perform one or more scans of a ROI of the patient. In addition, the operator may provide user inputs that initiate pre-programmed imaging sequences or protocols. Similarly, the operator may control the display of the resulting image on the display 442 and can perform image-enhancement functions using programs executed by the controller 440.

Figure 10:
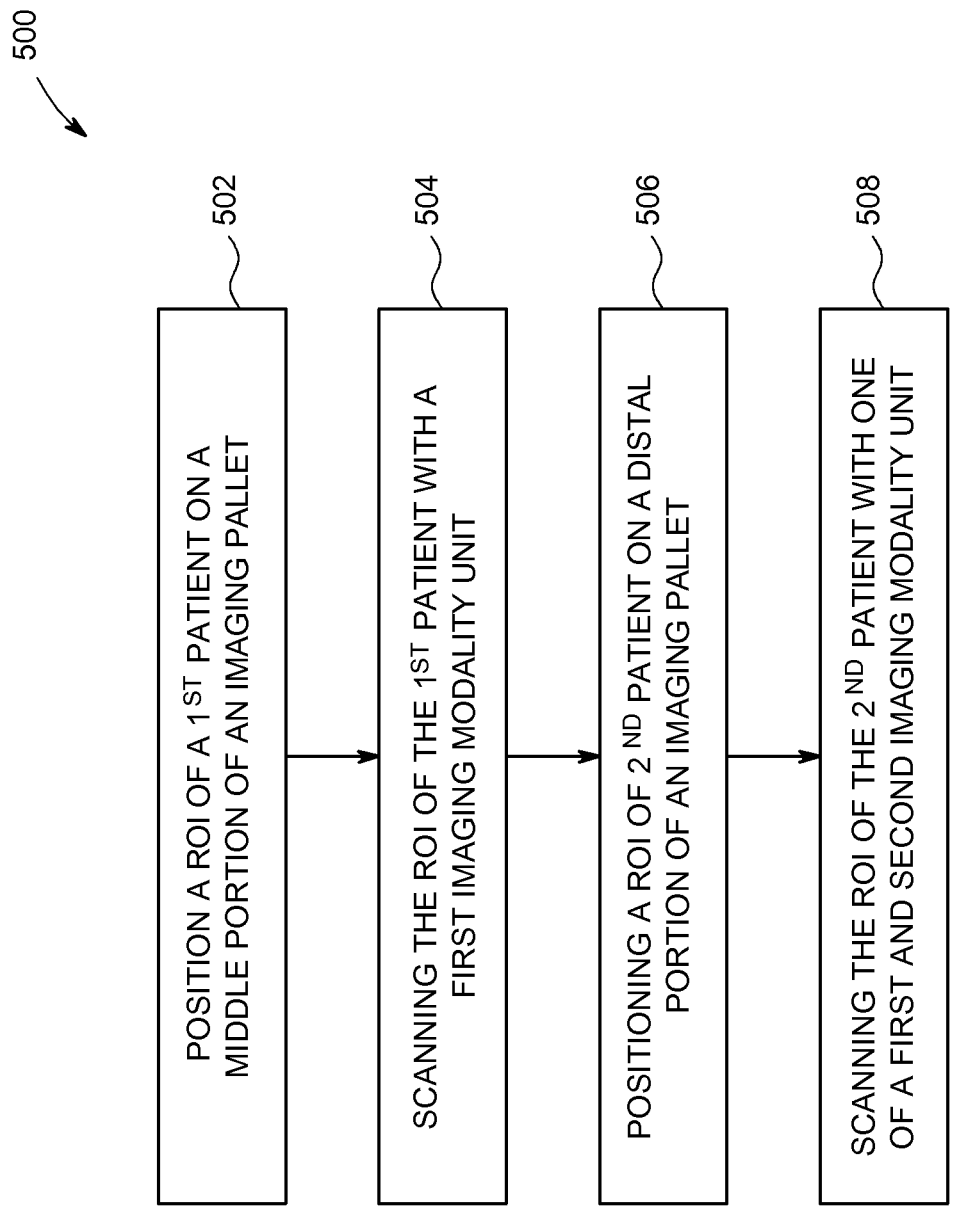
FIG. 10 is a block diagram of a method of operating an imaging system in accordance with various embodiments.

FIG. 10 is a block diagram of a method 500 for operating a multi-modality imaging system. In particular embodiments, the multi-modality imaging systems 100 and 400 are configured to perform the method 500. The imaging system may include a positioning system, such as the positioning systems 124 and 424 described above. The positioning system is configured to move patients through one or more imaging modality units. The imaging system may also include first and second imaging modality units that have respective FOVs. As shown in FIG. 10, the method 500 includes positioning, at 502, a region-of-interest (ROI) of a first patient on a middle portion of an imaging pallet of the positioning system. For example, the controller 440 may generate a set of commands that move the pallet along an examination axis into the FOV. The method 500 also includes scanning, at 504, the ROI of the first patient within the FOV of the first modality unit. As described above, the middle portion may have a cross-section that is configured for the first modality unit.

The method 500 also includes positioning, at 506, a ROI of a second patient on a distal portion of the pallet. The distal portion may be configured for the first modality unit or the second modality unit. More specifically, the distal portion may have an acceptable level of energy attenuation and/or artifacts within the acquired image. The method 500 also includes scanning, at 508, the ROI of the second patient at one of the FOVs of the first and second modality units. The distal portion may have a cross-section that is different than the cross-section of the middle portion.

In some embodiments, the scanning, at 508, of the ROI of the second patient includes scanning the ROI of the second patient within the FOV of the first modality unit. The ROI of the second patient may then be positioned within the FOV of the second modality unit. The ROI of the patient may then be scanned within the FOV of the second modality unit.

Figure 11:
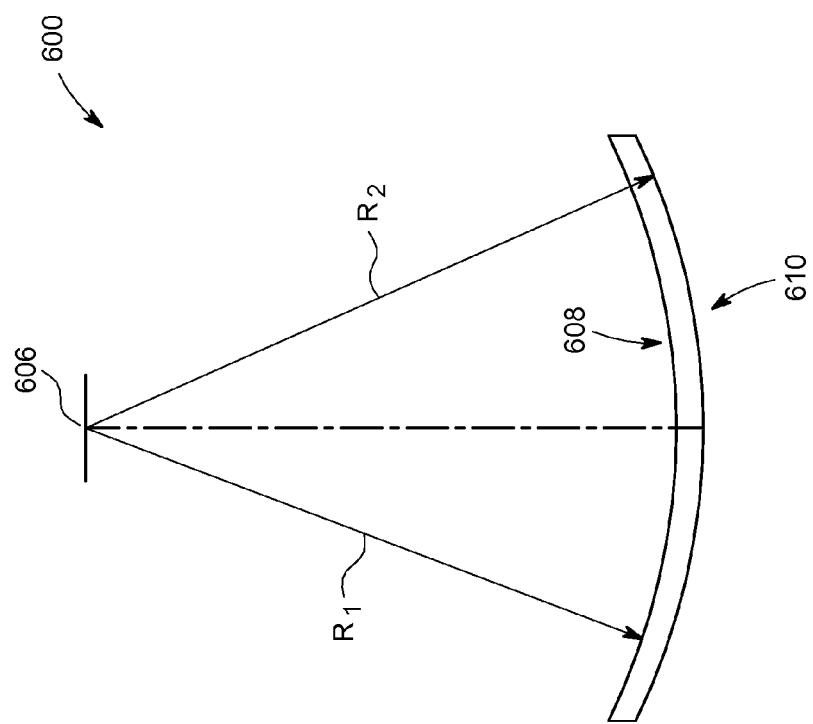
FIG. 11 illustrates a cross-section of a pallet that may be formed in accordance with another embodiment.

FIG. 11 illustrates a cross-section of a body portion 600 of a imaging pallet (not shown) that may be formed in accordance with another embodiment. The body portion 600 may be shaped for imaging by one or more modalities. For example, the body portion 600 may be shaped for imaging by both modality units 102 and 104 (FIG. 1). The body portion 600 may have a curved contour and a uniform thickness that curves about an axis 606. More specifically, the body portion 600 may have a thickness that extends between support and bottom surfaces 608 and 610. The support and bottom surfaces may have substantially equal radius-of-curvatures $R_1$ and $R_2$ about the axis 606.

In another embodiment, a method for operating a multi-modality imaging system is provided that includes imaging a single patient with the different modalities. For example, a ROI of the patient may be positioned on a body portion of an imaging pallet. The body portion may be similar to the distal portion 152 described above, and the imaging pallet may be similar to pallet 130 described above. The ROI may then be moved along an examination axis of the imaging system to the FOV of the first imaging modality unit. The ROI may then be scanned within the first imaging modality unit. The ROI may then be moved along the examination axis of the imaging system to the FOV of the second imaging modality unit and scanned there. Accordingly, the body portion may be configured or shaped for imaging within both the first and the second imaging modality units.

In another embodiment, a method of manufacturing an imaging pallet is provided. The pallet may comprise a common material throughout the body of the pallet. For example, the pallet may be manufactured by simultaneously forming the mounting portion, the middle portion, and the distal portion (as described above) within a mold. In some cases, an additional pallet skin (e.g., from carbon fibers) may be applied to the surfaces of the core. In other embodiments, the pallet may include different materials for the different body portions.

In another embodiment, a method of manufacturing a multi-modality imaging system is provided. The method includes positioning a plurality of imaging modality units and a positioning system having an imaging pallet with respect to each other. For example, the modality units may be aligned such that bores of the modality units are aligned along an examination axis. The positioning system may be configured to move the pallet along the examination axis. The pallet may be formed in accordance with various embodiments as described above with respect to the pallet 130.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A multi-modality imaging system comprising:
 a nuclear medicine (NM) modality unit and a computed-tomography (CT) modality unit, the NM and CT modality units having respective field of views (FOVs) spaced apart from each other; and
 a positioning system comprising a pallet support and an imaging pallet, the imaging pallet having an elongated support body that includes a mounting portion and first and second portions extending along a longitudinal axis of the support body, the mounting portion being mounted to the pallet support, the first portion extending between the mounting portion and the second portion and being shaped for imaging within the FOV of the NM modality unit, the second portion being shaped for imaging within the FOV of the CT modality unit, the first and second portions being shaped differently than each other and having first and second lengths, respectively, the second length being greater than the first length, wherein the positioning system is configured to position the first portion of the imaging pallet within the FOV of the NM modality unit while the mounting portion is mounted onto the pallet support and configured to position the second portion of the imaging pallet within the FOV of the CT modality unit while the mounting portion remains mounted onto the pallet support, wherein the FOVs of the NM and CT modality units are aligned with each other along an examination axis, the positioning system moving the imaging pallet along the examination axis to position the imaging pallet, wherein the first portion is shaped for the NM modality unit and is configured such that attenuation to 140 keV gamma rays does not exceed 10%, and wherein the second portion is shaped for the CT modality unit and is configured such that attenuation to 120 kVp X-ray does not exceed 27%.

2. The imaging system in accordance with claim 1 wherein the first portion has a plurality of cross-sections extending transverse to the longitudinal axis, the plurality of cross-sections including a medial cross-section that is proximate to the mounting portion and a distal cross-section that is proximate to the second portion, the medial and distal cross-sections having different dimensions, wherein a cross-sectional shape of the first portion reduces as the first portion extends from the medial cross-section to the distal cross-section, the first portion having a scan section located between the medial and distal cross-sections, the positioning system configured to position the scan section within the FOV of the NM modality unit.

3. The imaging system in accordance with claim 2 wherein the medial cross-section has a cross-sectional area that is greater than a cross-sectional area of the distal cross-section.

4. The imaging system in accordance with claim 1 wherein the imaging pallet has a bottom side, the bottom side having a width along the first portion that reduces as the first portion extends from the mounting portion toward the second portion, the width decreasing through a scan section of the first portion that extends between the mounting portion and the second portion, the positioning system configured to position the scan section within the FOV of the NM modality unit, wherein the imaging pallet has a support surface adapted to support a patient thereon, the support surface having a contour that is uniform through the first and second portions to a leading end of the support body.

5. The imaging system in accordance with claim 1 wherein the imaging pallet comprises a support surface adapted to support a patient thereon, the support surface having a curved contour that is uniform throughout the first and second portions from proximate to the mounting portion to a leading end of the support body.

6. The imaging system in accordance with claim 1 wherein the imaging pallet comprises a support surface adapted to support a patient thereon, the support surface having a contour that is uniform through the first and second portions to a leading end of the support body.

7. The imaging system in accordance with claim 1 wherein the imaging pallet comprises a support surface adapted to support a patient thereon, the support surface having a lowest point that extends lengthwise through the first and second portions, the imaging pallet having a thickness measured between the lowest point and a bottom surface of the imaging pallet that is substantially uniform throughout the first and second portions, the support body having a pallet length that extends between opposite first and second ends of the support body, the second length being greater than half of the pallet length.

8. The imaging system in accordance with claim 1 wherein the second portion of the support body is also shaped for imaging within the FOV of the NM modality unit.

9. The imaging system in accordance with claim 1 wherein the support body has a pallet length that extends between opposite first and second ends of the support body, the second length being greater than half of the pallet length.

10. The imaging system of claim 1, further comprising a controller configured to control operation of the positioning system, wherein the positioning system is configured to receive instructions from the controller for automatically moving the first portion of the imaging pallet within the FOV of the NM modality unit and configured to receive instructions from the controller for automatically moving the second portion of the imaging pallet within the FOV of the CT modality unit.

11. The imaging system of claim 1, wherein the first and second portions are shaped such that the first portion provides less attenuation, when imaged in the FOV of the NM modality unit, than attenuation provided by the second portion, if imaged in the FOV of the NM modality unit.

12. An imaging pallet for an imaging system, the imaging pallet comprising:
an elongated support body adapted to support a patient thereon during an imaging session, the support body having a pallet length that extends between opposite ends of the support body;
a mounting portion of the support body, the mounting portion configured to engage a positioning system of the imaging system;
a first portion of the support body extending lengthwise away from the mounting portion, the first portion being shaped for imaging within a field-of-view (FOV) of a nuclear medicine (NM) modality unit, the first portion having a first length; and
a second portion of the support body extending lengthwise away from the first portion, the first portion extending between the mounting and second portions, the second portion being shaped for imaging within a FOV of a computed tomography (CT) modality unit, the first and second portions having different shapes such that the second portion causes less attenuation, when imaged within the FOV of the CT imaging modality unit, than the first portion, when imaged within the FOV of the CT imaging modality unit, wherein the second portion has a second length that is greater than the first length and is greater than half of the pallet length, wherein the first portion is configured such that attenuation to 140 keV gamma rays does not exceed 10%, and wherein the second portion is configured such that attenuation to 120 kVp X-ray does not exceed 27%.

13. The imaging pallet in accordance with claim 12 wherein the first portion has a plurality of cross-sections extending laterally through the support body, the plurality of cross-sections including a medial cross-section that is proximate to the mounting portion and a distal cross-section that is proximate to the second portion, the medial and distal cross-sections having different dimensions, wherein a cross-sectional shape of the first portion reduces as the first portion extends from the medial cross-section to the distal cross-section.

14. The imaging pallet in accordance with claim 13 further comprising a bottom side, the bottom side having a width along the first portion that at least partially defines the cross-sectional shape of the first portion, the width reducing as the first portion extends from the medial cross-section to the distal cross-section.

15. The imaging pallet in accordance with claim 13 further comprising a support surface adapted to support a patient thereon, the support surface having a contour that is uniform through the first portion between the medial and distal cross-sections and through the second portion to a leading end of the support body.

16. The imaging pallet in accordance with claim 12 further comprising a support surface adapted to support a patient thereon, the support surface having a curved contour that is uniform throughout the first and second portions from proximate to the mounting portion to a leading end of the support body.

17. An imaging pallet for an imaging system, the imaging pallet comprising:
 an elongated support body adapted to support a patient thereon during an imaging session, the support body having a pallet length that extends between opposite ends of the support body;
 a mounting portion of the support body, the mounting portion configured to engage a positioning system of the imaging system;
 a first portion of the support body extending lengthwise away from the mounting portion, the first portion being shaped for imaging within a field-of-view (FOV) of a nuclear medicine (NM) modality unit; and
 a second portion of the support body extending lengthwise away from the first portion, the first portion extending between the mounting and second portions, the second portion being shaped for imaging within a FOV of a computed-tomography (CT) modality unit, the first and second portions having different shapes such that the second portion causes less attenuation, when imaged within the FOV of the CT modality unit, than the first portion, when imaged within the FOV of the CT modality unit, wherein the first portion is configured such that attenuation to 140 keV gamma rays does not exceed 10%, and wherein the second portion is configured such that attenuation to 120 kVp X-ray does not exceed 27%.

18. The imaging pallet in accordance with claim 17, wherein the imaging pallet comprises a support surface adapted to support a patient thereon, the support surface having a curved contour that is uniform throughout the first and second portions from proximate to the mounting portion to a leading end of the support body.

19. The imaging pallet in accordance with claim 17, wherein the second portion has a length that is greater than half of the pallet length.

20. The imaging pallet in accordance with claim 17, wherein the imaging pallet comprises a support surface adapted to support a patient thereon, the support surface having a lowest point that extends lengthwise through the first and second portions, the imaging pallet having a thickness measured between the lowest point and a bottom surface of the imaging pallet that is substantially uniform throughout the first and second portions.

21. The imaging pallet in accordance with claim 17, wherein the imaging pallet has a bottom side, the bottom side having a width along the first portion that reduces as the first portion extends from the mounting portion toward the second portion, the width decreasing through a scan section of the first portion that extends between the mounting portion and the second portion, wherein the imaging pallet has a support surface adapted to support a patient thereon, the support surface having a contour that is uniform through the first and second portions to a leading end of the support body.

22. The imaging pallet in accordance with claim 17, wherein the first portion has a plurality of cross-sections extending transverse to the longitudinal axis, the plurality of cross-sections including a medial cross-section that is proximate to the mounting portion and a distal cross-section that is proximate to the second portion, the medial and distal cross-sections having different dimensions, wherein a cross-sectional shape of the first portion reduces as the first portion extends from the medial cross-section to the distal cross-section.

* * * * *